United States Patent
Bolze et al.

(10) Patent No.: US 7,364,554 B2
(45) Date of Patent: Apr. 29, 2008

(54) APPARATUS FOR ADMINISTERING ACOUSTIC SHOCK WAVES HAVING A REMOVABLE AND REPLACEABLE COMPONENT WITH A DATA STORAGE MEDIUM

(75) Inventors: Rüdiger Bolze, Reichenau (DE); Norbert Brill, Constance (DE)

(73) Assignee: SanuWave, Inc., Alpharetta, GA (US)

( * ) Notice: Subject to any disclaimer, the term of this patent is extended or adjusted under 35 U.S.C. 154(b) by 191 days.

(21) Appl. No.: 10/154,393

(22) Filed: May 23, 2002

(65) Prior Publication Data

US 2002/0193709 A1 Dec. 19, 2002

(30) Foreign Application Priority Data

May 23, 2001 (DE) .................. 101 25 936

(51) Int. Cl.
*A61H 1/00* (2006.01)
(52) U.S. Cl. ............................... 601/2; 601/4
(58) Field of Classification Search ............... 100/437, 100/439; 601/2–4; 65/2, 3; 600/407, 437–439, 600/459, 472, 300–302, 462–471; 73/625, 73/626, 620, 1.01, 35.14, 570; 348/163; 439/488; 702/65, 85
See application file for complete search history.

(56) References Cited

U.S. PATENT DOCUMENTS

| | | | | |
|---|---|---|---|---|
| 4,791,915 A * | 12/1988 | Barsotti et al. ................. | 601/2 |
| 4,868,476 A * | 9/1989 | Respaut ........................ | 318/632 |
| 4,957,100 A * | 9/1990 | Herzog et al. .................. | 601/2 |
| 4,972,470 A * | 11/1990 | Farago ......................... | 713/192 |
| 5,095,908 A * | 3/1992 | Belikan et al. ................. | 600/439 |
| 5,251,631 A * | 10/1993 | Tsuchiko et al. ............... | 600/447 |
| 5,287,856 A | 2/1994 | Treiber .................... | 128/660.03 |
| 5,400,267 A * | 3/1995 | Denen et al. ................... | 702/59 |
| 5,425,375 A * | 6/1995 | Chin et al. .................... | 600/549 |
| 5,487,386 A * | 1/1996 | Wakabayashi et al. .......... | 600/437 |
| 5,564,108 A * | 10/1996 | Hunsaker et al. .............. | 702/65 |
| 5,603,323 A * | 2/1997 | Pflugrath et al. ............. | 600/437 |
| 5,615,344 A * | 3/1997 | Corder ........................ | 710/62 |
| 5,835,897 A * | 11/1998 | Dang ........................... | 705/2 |
| 6,036,661 A * | 3/2000 | Schwarze et al. .............. | 601/4 |
| 6,063,030 A * | 5/2000 | Vara et al. .................... | 600/437 |
| 6,080,119 A | 6/2000 | Schwarze et al. .............. | 601/4 |
| 6,092,722 A | 7/2000 | Heinrichs et al. ............ | 235/375 |
| 6,113,560 A | 9/2000 | Simnacher ..................... | 601/4 |
| 6,243,654 B1* | 6/2001 | Johnson et al. ................ | 702/85 |
| 6,298,255 B1* | 10/2001 | Cordero et al. .............. | 600/372 |
| 6,370,511 B1* | 4/2002 | Dang ........................... | 705/3 |
| 6,464,636 B1* | 10/2002 | Kinicki et al. ............... | 600/437 |
| 6,585,660 B2* | 7/2003 | Dorando et al. .............. | 600/486 |
| 6,602,227 B1* | 8/2003 | Cimino et al. ............... | 604/113 |
| 6,787,974 B2* | 9/2004 | Fjield et al. ................. | 310/335 |
| 2002/0032584 A1* | 3/2002 | Doctor et al. .................. | 705/3 |
| 2002/0087362 A1* | 7/2002 | Cobb et al. .................... | 705/3 |

FOREIGN PATENT DOCUMENTS

GB 1073739 6/1967

* cited by examiner

*Primary Examiner*—Francis J. Jaworski
(74) *Attorney, Agent, or Firm*—Hunton & Williams LLP

(57) ABSTRACT

A medical device is described, which comprises a basic device and at least one replaceable component connected therewith, said component having an item belonging to the device that is subjected to high wear or consumption. A storage medium is connected to the component, which stores component-specific data and can be read independently of the basic device.

27 Claims, 1 Drawing Sheet

APPARATUS FOR ADMINISTERING ACOUSTIC SHOCK WAVES HAVING A REMOVABLE AND REPLACEABLE COMPONENT WITH A DATA STORAGE MEDIUM

BACKGROUND OF THE INVENTION

The present invention relates to the field of medical devices for delivering acoustic shock waves, and in particular to a device for delivering acoustic shock waves having a removable, replaceable component with a data storage unit.

Medical devices frequently have items exposed to a great deal of wear or consumption. Therefore, it is desirable to place these high-wear items in separate removable and replaceable components connected with the basic device and replace them when necessary. In general, these components are identified by the manufacturer's embossed serial and/or lot numbers. This identification is documented at the manufacturing facility before delivery. Thus, while the component can be traced if it is returned to the manufacturer, no information is provided on the wear of the component during operation of the medical device.

To ensure the necessary safety when medical devices are in operation, it is necessary for the manufacturer and/or operator of the device to be continuously informed of the status of all the device components. This is particularly important for liability issues. It is especially important to replace parts that are consumable or exposed to wear promptly. Because wear and consumption are heavily dependent on the use of the device, for safety reasons replacement is usually done early and at fixed intervals regardless of actual use. This runs counter to economical use of the device components.

U.S. Pat. No. 6,036,661 assigned to the assignee of the present invention discloses a medical device for application of acoustic shock waves in which a replaceable treatment head connected with a basic device has a memory that can be read by the basic device so that the operating values of the basic device can be adjusted to the specific treatment head being used. In addition, usage data on the treatment head such as total operating time, number of shots, and number of shots remaining for the service life are stored, and are read, processed, and displayed by the basic device. However, data exchange to and from the treatment head memory is possible only through the basic device.

Therefore, there is a need for a replaceable component such as for example a treatment head that stores usage data of the component, and can download/transmit data from the component head.

SUMMARY OF THE INVENTION

Briefly, according to an aspect of the invention, a removable and replaceable component for use in a device for delivering acoustic shock waves includes a storage medium that stores component usage information.

According to another aspect of the invention, a removable and replaceable component for use in a device for delivering acoustic shock waves includes a storage medium that stores component identification information.

The information within the component storage medium can be read from the component, even while the component is removed from the device for delivering acoustic shock waves. The component may be for example a treatment head, and/or a power supply unit. A basic idea of the invention is to place the replaceable items of the device that are exposed to wear or consumption in separate components, and provide them with a storage medium that stores information relevant to the component and its use, which can be read from the removable and replaceable component independently of the basic device via for example a standardized interface. The interface may be associated with a wireline or wireless communication channel.

The relevant information can be read from the component (e.g., a treatment head) even when the component is not mounted on the basic device. As a result, removable and replaceable components can be easily inventoried to determine for example the use information for each of the treatment heads in inventory. It is thus possible to ensure that the components are available in the proper number, are procured on time, and are serviced or reprocessed promptly, with economically optimal use of the components.

The operationally relevant information can also be read by the manufacturer from the memory of the component returned for repair or reprocessing. This facilitates improved quality management by the manufacturer. This information can also be evaluated for manufacturing logistics to document, evaluate, and optimize manufacturing, storage, delivery, reprocessing, etc.

The relevant information can also be read by the user at the site where the device is used and forwarded to the manufacturer without the component having to be shipped. If such data transfers are done at regular intervals, the manufacturer can perform remote maintenance. The user can be promptly alerted about necessary servicing and reprocessing tasks, thus facilitating planning by the manufacturer and operator.

Reading the component memory externally also makes it possible to document device use continuously. While using the device, the physician can read and document the treatment measures performed by the device as they relate to the patient. It is also possible for leases of such devices to be based on actual use of the device, rather than time. For example, the use information can be read by the user and transmitted to the device owner for billing purposes via the Internet, e-mail, or a data carrier, for example.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
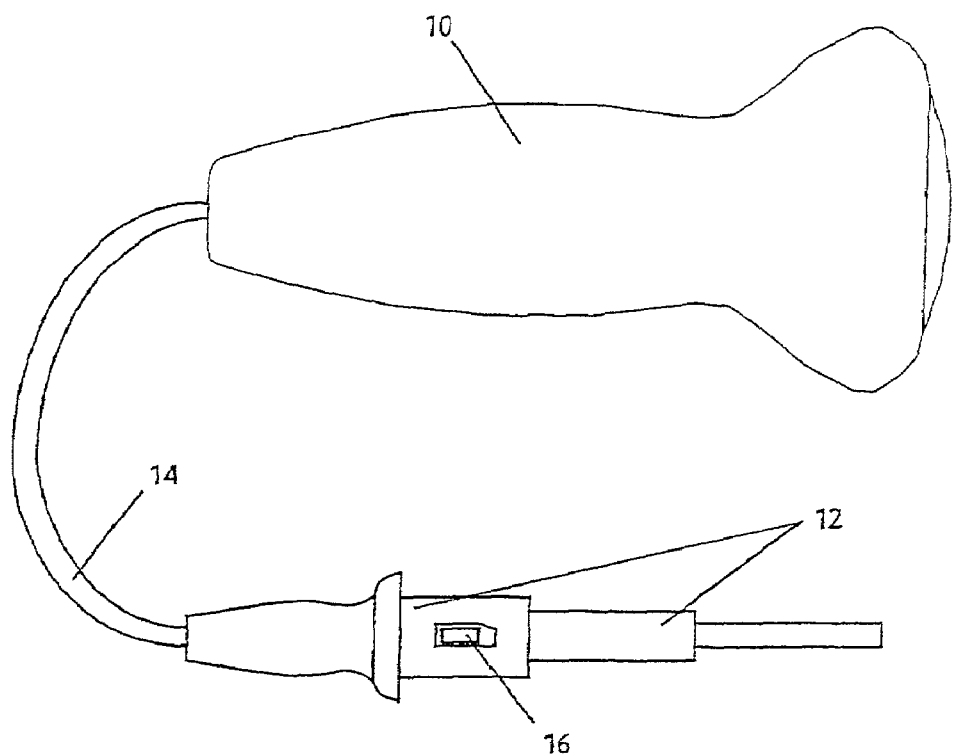
FIG. 1 is a pictorial illustration of a removable and replaceable treatment head having a storage medium for use in a device for delivering acoustic shock waves.

FIG. 1 is a pictorial illustration of a removable and replaceable treatment head 10 having a storage medium 16 for use in a device for generating acoustic shock waves for extracorporeal shock wave therapy. The treatment therapy head 10 includes electrodes, for example for electrohydraulic shock wave generation, between which there is an electrical spark discharge. This causes the electrodes to be consumed, such that after a certain number of spark discharges the treatment head 10 has to be reprocessed. The treatment head 10 is connected via a cable 14 and a plug 12 to a basic device, not shown. U.S. Pat. No. 6,036,661 incorporated herein by reference and assigned to the assignee of the present invention, illustrates a removable treatment head connected to a basic unit. The basic device contains the power supply and control for the treatment head 10.

The storage medium 16 is mounted on the part of plug 12 connected to the treatment head 10. The attachment of the storage medium 16 to the treatment head 10 (e.g., the plug of the therapy head) is fixed so that the storage medium 16 is continuously connected to the plug 12 of the treatment head. The storage medium 16 is preferably a read-write memory. An optical memory (CD-R, CD-R/W), an electric flash card, a magnetic storage card, or a smart card for example can be used as the storage medium. In one embodiment, the storage medium 16 is configured as a chip card attached to the plug 12 of the treatment head 10.

Data can be read from the storage medium 16, and data can be written from the basic device into the storage medium 16. If the plug 12 is separate, the treatment head 10 can be connected via this interface to an independent reader or a data carrier. In this way, the data stored in the storage medium 16 can be read independently of the basic device. It is also possible to write data to the storage medium 16 independently of the basic device.

Figure 2:
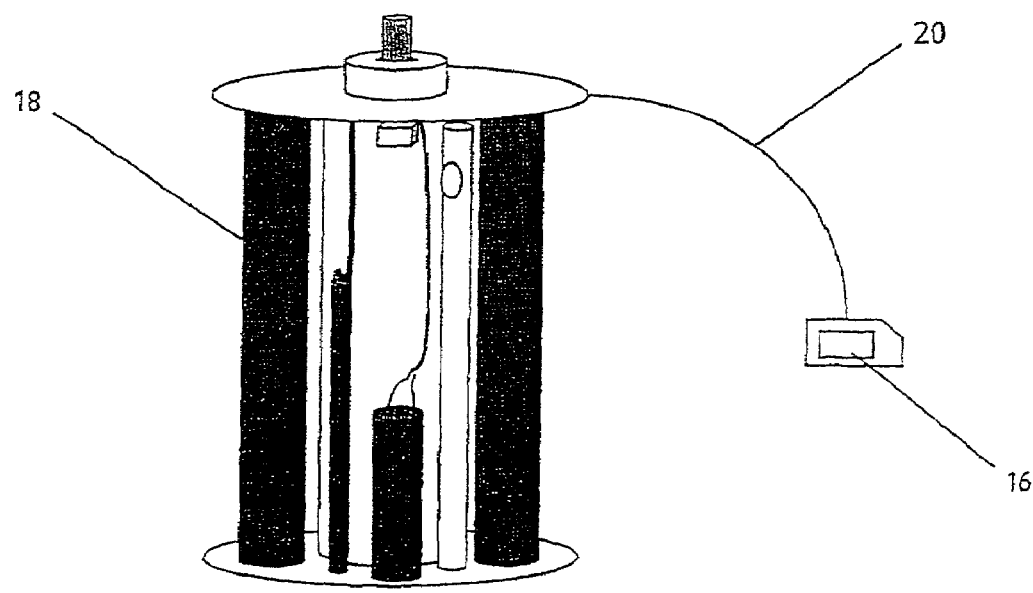
FIG. 2 is a pictorial illustration of a removable and replaceable power supply unit having a storage medium for use in a device for delivering acoustic shock waves.

The removable and replaceable component shown in FIG. 2 is a removable and replaceable power supply 18 of a device for generating acoustic shock waves. The power supply 18 is configured as a replaceable cartridge that is inserted into the basic device, and supplies for example the treatment head 10 illustrated in FIG. 1. The power supply 18 includes a charging capacitor and a spark gap serving as a high-voltage switch. The spark gap is subjected to heavy wear, and as a result the power supply 18 has to be reprocessed or replaced after a certain amount of use.

As shown in FIG. 2, the storage medium 16 is permanently connected to the cartridge of the power supply 18 via a flexible connecting element 20, such as for example a cord, a wire, or a cable. In one embodiment, the storage medium 16 is provided with a separate interface and can be inserted into a corresponding socket either of the basic device or of a separate reader or data transmitting device.

The storage medium 16 may include the serial number and batch number of the removable and replaceable component that it is associated with. For example, if the storage medium is associated with the treatment head as shown in FIG. 1, then the storage medium may include the serial number and batch number of that treatment head.

The information may also include the serial number and batch number of the basic device into which the component is placed. In addition, any other information/parameters of the component (e.g., 10 or 18) that identify its properties and method of operation may also be stored in the storage medium. This information is preferably entered into the storage medium 16 by the manufacturer and continues unchanged.

The storage medium 16 may include information documenting the use of the removable and replaceable component. The stored information may also include for example the current model version, and information on any servicing or reprocessing. This information is preferably entered by the manufacturer or service organization. In addition, information indicative of the use of the removable and replaceable component, such as for example the number, duration, and operating parameters of use may also be stored in the storage medium. This information can be entered into the storage unit either by the component itself and/or by the basic unit. If the component is a treatment head 10, this information can be used for documentation of the medical treatment and for billing use.

Although the present invention has been shown and described with respect to several preferred embodiments thereof, various changes, omissions and additions to the form and detail thereof, may be made therein, without departing from the spirit and scope of the invention.

What is claimed is:

1. A medical device comprising a basic device and at least one replaceable electrically powered component subject to wear or consumption in generation of acoustic shockwaves and connectable to the basic device, wherein the component comprises a memory device that stores component-specific data indicative of the wear and consumption of the component for documentation and billing of treatment performed with the component, wherein the component-specific data can be read from the memory device by an external reader independently of data exchange between the memory device and a reader of the basic device.

2. Device according to claim 1, wherein that the memory device is permanently mounted on said component.

3. Device according to claim 2, wherein the memory device comprises a read-write memory.

4. Device according to claim 3, wherein the memory device can be read via a plug-in interface.

5. Device according to claim 4, wherein the memory device can be connected via the plug-in interface to a basic device on the one hand and to an independent reader or data transmission device on the other hand.

6. Device according to claim 5, wherein the component is connectable with the basic device via a plug.

7. Device according to claim 2, wherein the memory device is built into the component.

8. Device according to claim 2, wherein the memory device is connected via a flexible connecting element to the component.

9. Device according to claim 1, wherein data identifying the component are stored in the memory device.

10. Device according to claim 1, wherein operating and usage data indicative of servicing, maintenance, and reprocessing of the component are stored in the memory device.

11. A removable medical device component configured and arranged to be used in a device for generating acoustic shockwaves, said medical device component comprising:
an electrically powered component subject to wear or consumption in the generation of acoustic shockwaves; and
a memory device connected to an external standardized data interface independent of a basic device controlling the component through which component-specific data indicative of the wear and consumption of the electrically powered component can be read from said memory device.

12. The device of claim 11, wherein said memory device is permanently mounted on said electrically powered component.

13. The device of claim 12, wherein said memory device is a read-write memory.

14. The device of claim 13, wherein said memory device can be read via a plug-in data interface.

15. The device of claim 14, wherein said memory device is adapted to be connected via the data interface to a basic device on the one hand and to an independent reader or data transmission device on the other hand.

16. The device of claim 15, wherein said memory device comprises an optical memory device.

17. The device of claim 15, wherein said memory device comprises a flash card memory device.

18. The device of claim 15, wherein said memory device comprises a magnetic storage device.

19. The device of claim 15, wherein said memory device comprises a smart card.

20. The device of claim 11, wherein data identifying the component are stored in the memory device.

21. The device of claim 11, wherein component-specific data indicative of servicing, maintenance, and reprocessing of the component are stored in the memory device.

22. The device of claim 11, wherein component-specific data indicative of the wear and consumption of the component are stored in the memory device for documentation and billing of the treatments performed with the medical device component.

23. A removable and replaceable electrical component for use in a medical device for generating and administering acoustic shock waves to a patient, said removable and replaceable component comprising:

an electrical operating element that is configured and arranged to be electrically and operably connected to the medical device for generating and administering acoustic shock waves; coupling means between the electrical component and a basic device controlling the electrical component and a non-volatile memory device independently readable apart from by the basic device that contains information indicative of the usage and identification of said removable and replaceable electrical component.

24. The removable and replaceable electrical component of claim 23, wherein said electrical operating element comprises a power supply.

25. The removable and replaceable electrical component of claim 23, wherein said electrical operating element comprises an electrohydraulic shock wave therapy head.

26. The removable and replaceable electrical component of claim 23, comprising a wireline interface through which the information indicative of the usage and identification of said removable and replaceable electrical component can be read from said memory device.

27. The removable and replaceable electrical component of claim 23, wherein the information indicative of the usage and identification of said removable and replaceable electrical component comprises data indicative of the number of uses, the duration of use, and operating parameters indicative of the use.

* * * * *